United States Patent
Lee et al.

(10) Patent No.: US 9,386,956 B2
(45) Date of Patent: Jul. 12, 2016

(54) X-RAY IMAGING APPARATUS, X-RAY IMAGE GENERATION METHOD, AND 3D IMAGING APPARATUS

(71) Applicant: SAMSUNG ELECTRONICS CO., LTD., Suwon-si (KR)

(72) Inventors: Jae Hak Lee, Yongin-si (KR); Young Hun Sung, Hwaseong-si (KR); Kang Eui Lee, Seoul (KR); Jong Ha Lee, Hwaseong-si (KR); Kwang Eun Jang, Busan (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 251 days.

(21) Appl. No.: 14/104,295

(22) Filed: Dec. 12, 2013

(65) Prior Publication Data

US 2014/0185749 A1    Jul. 3, 2014

(30) Foreign Application Priority Data

Dec. 28, 2012  (KR) .......................... 10-2012-0156255

(51) Int. Cl.
```
G06T 15/00    (2011.01)
A61B 6/02     (2006.01)
A61B 6/04     (2006.01)
A61B 6/00     (2006.01)
G06T 11/00    (2006.01)
```

(52) U.S. Cl.
CPC ............... *A61B 6/025* (2013.01); *A61B 6/0414* (2013.01); *A61B 6/502* (2013.01); *A61B 6/5205* (2013.01); *G06T 11/006* (2013.01); *G06T 11/008* (2013.01); *A61B 6/588* (2013.01)

(58) Field of Classification Search
CPC .... G06T 11/006; G06T 11/008; A61B 6/025; A61B 6/588; A61B 6/502; A61B 6/5205; A61B 6/0414
USPC .............................. 345/424, 422, 419; 378/41
See application file for complete search history.

(56) References Cited

U.S. PATENT DOCUMENTS

| | | | |
|---|---|---|---|
| 7,668,285 B2 | 2/2010 | Mukumoto | |
| 7,873,142 B2* | 1/2011 | Beets | A61B 6/4441 378/146 |
| 8,189,735 B2* | 5/2012 | Khare | G06T 11/006 378/4 |
| 8,422,764 B2* | 4/2013 | Ye | G06T 11/006 382/154 |
| 8,630,472 B2* | 1/2014 | Kunze | A61B 6/032 378/11 |
| 2012/0020448 A1 | 1/2012 | Khare et al. | |

FOREIGN PATENT DOCUMENTS

| | | |
|---|---|---|
| JP | 2008-253803 A | 10/2008 |
| JP | 2009-195483 A | 9/2009 |

* cited by examiner

*Primary Examiner* — Phu K Nguyen
(74) *Attorney, Agent, or Firm* — Sughrue Mion, PLLC

(57) ABSTRACT

The X-ray imaging apparatus includes an X-ray source that emits X-rays to an object at different original-view positions, an X-ray detector that acquires original-view images by detecting X-rays having passed through the object, and an image controller that reconstructs a 3D volume image representation of the object from the original-view images and generates close-view images by virtually emitting X-rays to the 3D volume image representation of the object at a shorter distance than a distance between the X-ray source and the object.

20 Claims, 17 Drawing Sheets

X-RAY IMAGING APPARATUS, X-RAY IMAGE GENERATION METHOD, AND 3D IMAGING APPARATUS

CROSS-REFERENCE TO RELATED APPLICATION

This application claims priority from Korean Patent Application No. 10-2012-0156255, filed on Dec. 28, 2012 in the Korean Intellectual Property Office, the disclosure of which is incorporated herein by reference in its entirety.

BACKGROUND

1. Field

Apparatuses and methods consistent with exemplary embodiments to an X-ray imaging apparatus and an X-ray image generation method, which generate a three-dimensional (3D) X-ray image of an object by transmitting X-rays through the object.

2. Description of the Related Art

An X-ray imaging apparatus is used to determine an internal structure of an object by emitting X-rays to an object and analyzing X-rays having passed through the object. Transmittance of X-rays varies according to the tissues of the object, and therefore the internal structure of the object may be imaged using an attenuation coefficient that digitizes the varying transmittance.

Although the internal structure of the object may be imaged using three-dimensional (2D) images, there is a limit as to discrimination between normal tissues and diseased tissues using only 2D X-ray images. To compensate for this limit, a tomosynthesis system has been developed, in which images of an object are captured at different angles or different views via movement of an X-ray source to acquire a 3D X-ray image.

A 3D X-ray image facilitates easy discrimination between normal tissues and diseased tissues, and enables determination of morphological characteristics of an object, thereby being efficiently used in the medical field and the like. In the tomosynthesis system, enhancing 3D effects of a 3D X-ray image may be desired because enhanced 3D effects of a 3D X-ray image help to provide more accurate diagnosis.

SUMMARY

Exemplary embodiments may address at least the above problems and/or disadvantages and other disadvantages not described above. Also, the exemplary embodiments are not required to overcome the disadvantages described above, and an exemplary embodiment may not overcome any of the problems described above.

One or more embodiments provide a 3D X-ray image having enhanced 3D effects by generating a virtual close-view image corresponding to the case of assuming that X-rays are emitted to an object at a shorter distance than a real distance, and generating a 3D X-ray image of the object using the generated close-view image.

In accordance with an aspect of an exemplary embodiment, an X-ray imaging apparatus includes an X-ray source that emits X-rays to an object at a plurality of different original-views, an X-ray detector that acquires a plurality of original-view images by detecting X-rays having passed through the object, and an image controller that reconstructs a 3D volume of the object from the plurality of original-view images and generates a plurality of close-view images by virtually emitting X-rays to the 3D volume of the object at a shorter distance than a distance between the X-ray source and the object.

The image controller may include a middle-view image generator that generates middle-view images corresponding to middle views located between the plurality of original-views.

The image controller may further include a 3D reconstructor that reconstructs the 3D volume of the object from the plurality of original-view images and the middle-view images using a 3D reconstruction method.

The image controller may further include a close-view image generator that generates the close-view images by virtually emitting X-rays to the 3D volume of the object at the shorter distance than the distance between the X-ray source and the object via reprojection.

The X-ray imaging apparatus may further include an image processor that generates a 3D image of the object using the plurality of close-view images.

The X-ray imaging apparatus may further include a display that displays the 3D image generated by the image processor in a 3D manner.

In accordance with another aspect of an exemplary embodiment, an X-ray image generation method includes emitting X-rays to an object at different original-views, acquiring a plurality of original-view images by detecting X-rays having passed through the object, reconstructing a 3D volume of the object from the plurality of original-view images, and generating a plurality of close-view images by virtually emitting X-rays to the 3D volume of the object at a shorter distance than an X-ray emission distance to the object.

The X-ray image generation method may further include generating middle-view images corresponding to middle views located between the plurality of original-views from the plurality of original-view images.

Reconstruction of the 3D volume of the object may include reconstructing the 3D volume of the object using the plurality of original-view images and the middle-view images.

The X-ray image generation method may further include generating a 3D image of the object using the plurality of generated close-view images.

The X-ray image generation method may further include displaying the 3D image of the object on a 3D display.

In accordance with a further aspect of an exemplary embodiment, a 3D imaging apparatus includes an image receiver that receives a plurality of original-view images acquired at different original-view positions, a 3D reconstructor that reconstructs a 3D volume of an object from the plurality of original-view images, and a close-view image generator that generates a plurality of virtual close-view images under the assumption that the 3D volume of the object is captured at a shorter distance than a distance between each view and the object.

BRIEF DESCRIPTION OF THE DRAWINGS

The above and/or other aspects will become more apparent by describing certain exemplary embodiments, with the accompanying drawings, in which.

DETAILED DESCRIPTION

Figure 1:
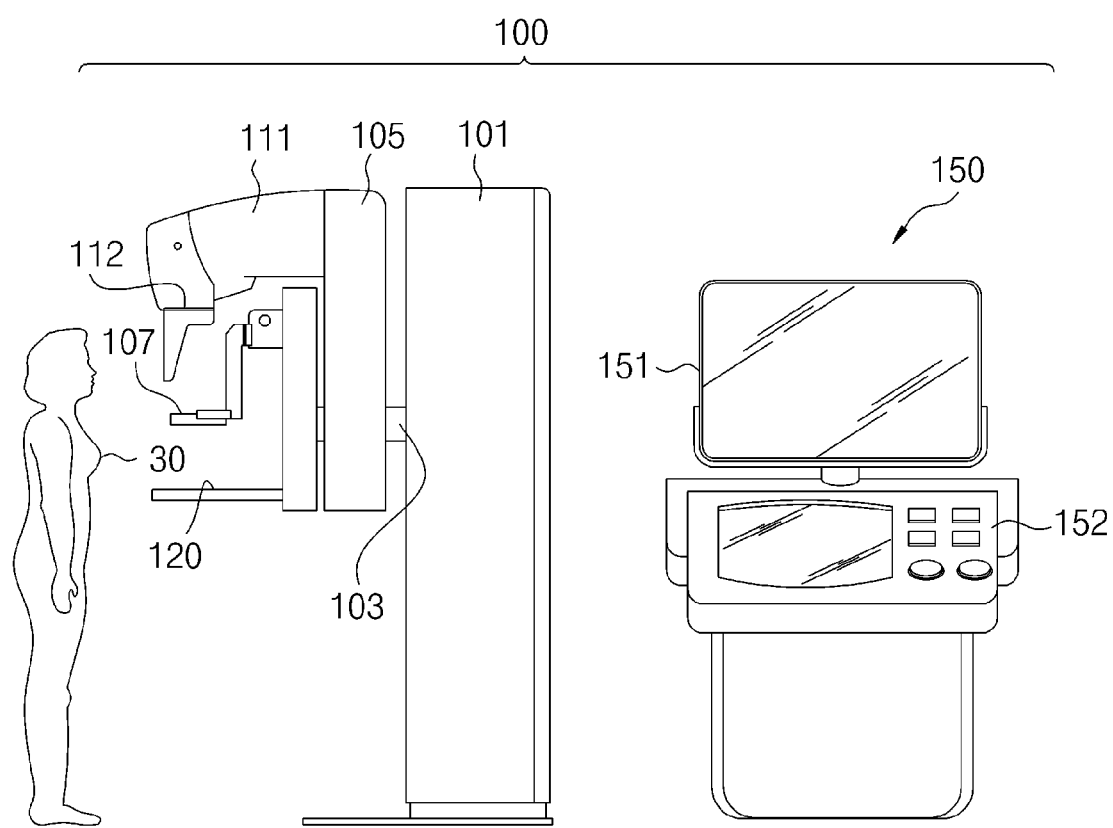
FIG. 1 is a view illustrating an overall external appearance of an X-ray imaging apparatus according to an exemplary embodiment.

Certain exemplary embodiments are described in greater detail below with reference to the accompanying drawings.

In the following description, the same drawing reference numerals are used for the same elements even in different drawings. The matters defined in the description, such as detailed construction and elements, are provided to assist in a comprehensive understanding of exemplary embodiments. Thus, it is apparent that exemplary embodiments can be carried out without those specifically defined matters. Also, well-known functions or constructions are not described in detail since they would obscure exemplary embodiments with unnecessary detail.

In an X-ray imaging apparatus according to an exemplary embodiment, a tomosynthesis method of acquiring 2D images of an object at different views respectively and generating a 3D image using the acquired 2D images is applied. Examples of the X-ray imaging apparatus according to the aspect may include a general X-ray apparatus, a mammography apparatus, and a Computed Tomography (CT) apparatus so long as the tomosynthesis method may be applied.

X-ray imaging apparatuses may be used to capture images of the chest, the mouth, the breast, and various bones of a human body according to a diagnosis purpose thereof, and configurations thereof may be slightly different according to imaging parts. Although there is no limit as to the kind of the object, i.e., parts to be captured by the X-ray imaging apparatus according to the aspect, for convenience of description, operations of an X-ray mammography apparatus to capture an image of the breast will be described by way of example in the exemplary embodiments.

FIG. 1 is a view illustrating an overall external appearance of an X-ray imaging apparatus according to an exemplary embodiment.

Referring to FIG. 1, the X-ray imaging apparatus 100 includes an X-ray source 111 to generate and emit X-rays to an object 30, an X-ray detector 120 to detect X-rays having passed through the object 30, a compression paddle 107 to compress the object 30, i.e., breast placed on the X-ray detector 120, a main body 101 to support the aforementioned components, and a host device 150 having a user interface.

More specifically, the X-ray source 111 generates X-rays and emits the X-rays outward through a window 112. When the object 30 is placed on the X-ray detector 120, the compression paddle 107 compresses the object 30 to a predetermined thickness, and X-rays emitted through the window 112 pass through the object 30 to thereby be detected by the X-ray detector 120.

The X-ray source 111 consists of an X-ray tube that generates X-rays and a housing that encloses the X-ray tube. The X-ray source 111 is also referred to as an X-ray tube head. The X-ray source 111 is connected to the main body 101 via an arm 105, and the arm 105 is rotatable about a rotating shaft 103 by a predetermined angle. When the arm 105 is rotated, the X-ray source 111 connected to the arm 105 is circularly moved. An overall rotation angle of the arm 105 or an angle corresponding to a view for emission of X-rays to the object 30 may be input by the user via an input unit 152 provided in the user workstation 150.

Figure 2:
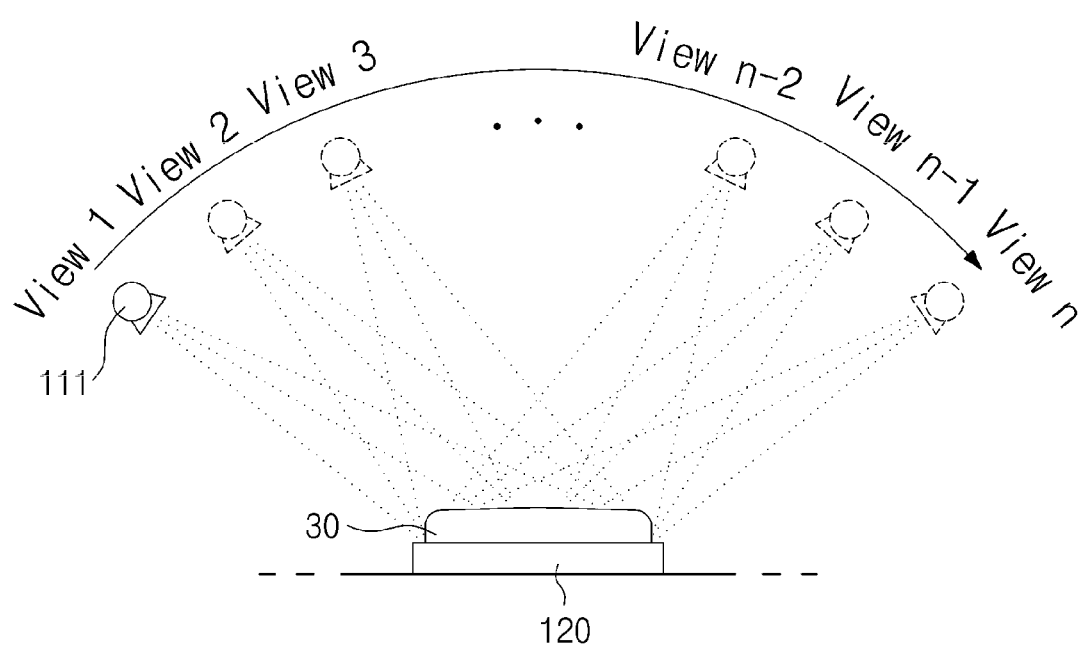
FIG. 2 is a view diagrammatically illustrating view variation depending on circular movement of an X-ray source in the X-ray imaging apparatus of FIG. 1.

FIG. 2 is a view diagrammatically illustrating view variation depending on circular movement of the X-ray source in the X-ray imaging apparatus of FIG. 1.

As illustrated in FIG. 2, a plurality of view images may be acquired by emitting X-rays to the object 30 at view 1 to view n via leftward movement of the X-ray source 111. Here, "view" refers to a position where a viewer views the object 30, or an X-ray imaging position of the object 30, i.e., a position where X-rays are emitted to the object 30. "View image" refers to an image acquired by emitting X-rays to the object 30 at a predetermined view. In the following embodiment, to discriminate virtual views, such as a middle-view, a close-view, etc., from a real X-ray imaging view, a real X-ray emission view may be referred to as an original-view.

A 3D image acquired by synthesizing a plurality of view images is displayed via a display 151 provided in the user workstation 150. The display 151 is a 3D display device to display a 3D image in a stereoscopic manner.

In the X-ray imaging apparatus 100 of FIG. 1, the arm 105 is connected to the X-ray source 111, but is not connected to the X-ray detector 120. Thus, when the arm 105 is rotated as illustrated in FIG. 2, only the X-ray source 111 is moved along with the arm 105, and the X-ray detector 120 is fixed to the main body 101. The tomosynthesis method mainly adopts a stationary X-ray detector, which may simplify a drive unit because it may be unnecessary to rotate the X-ray detector, and may be advantageous in terms of space utilization.

Figure 3:
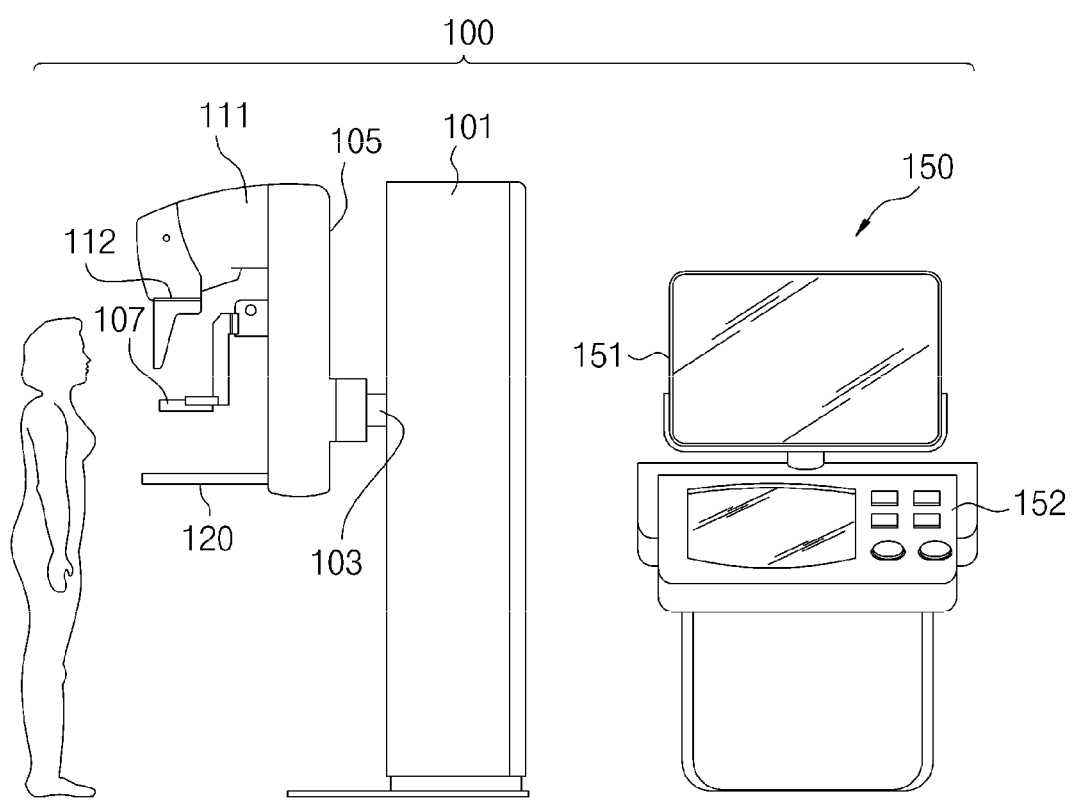
FIG. 3 is a view illustrating an overall external appearance of an X-ray imaging apparatus having a rotatable X-ray detector according to an exemplary embodiment.
Figure 4A:
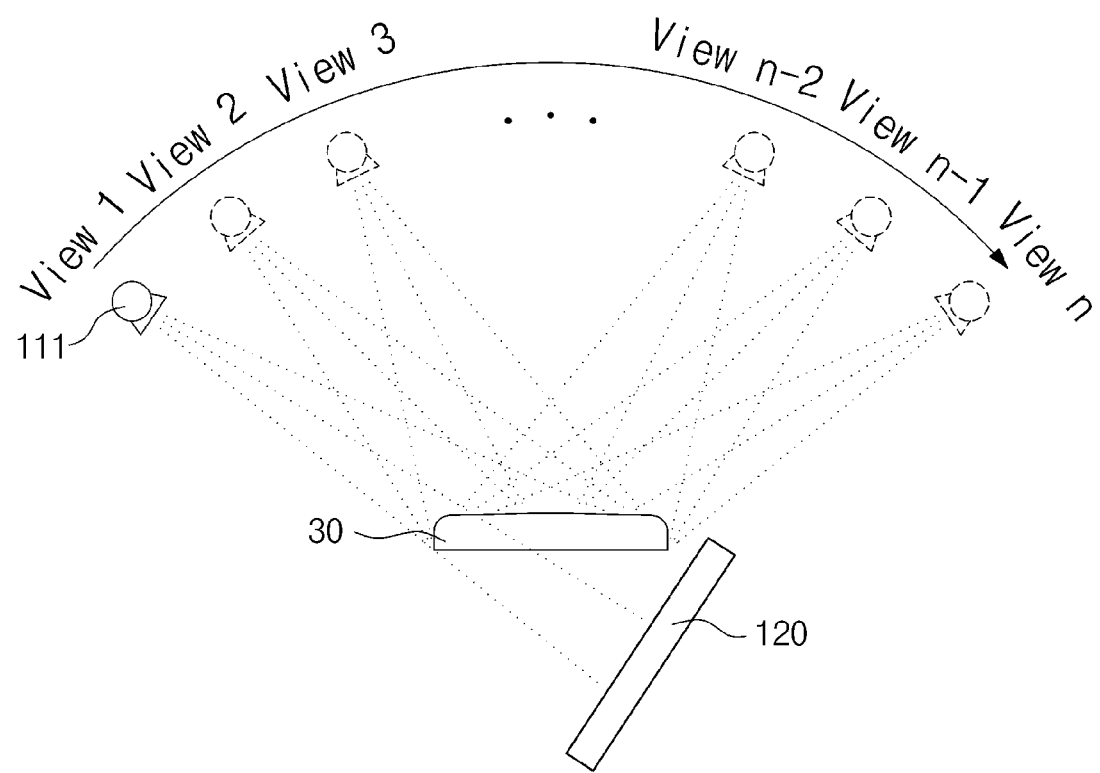
FIGS. 4A, 4B, 4C, and 4D are views diagrammatically illustrating view variation depending on circular movement of an X-ray source in the X-ray imaging apparatus of FIG. 3.
Figure 4B:
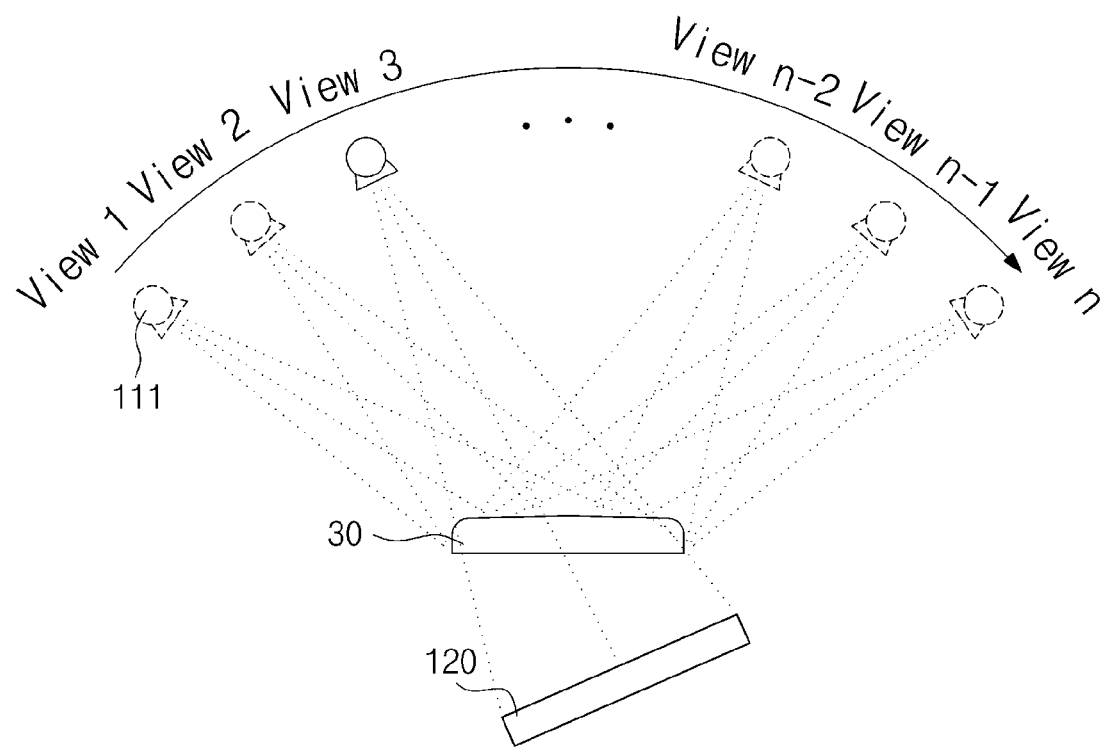
Figure 4C:
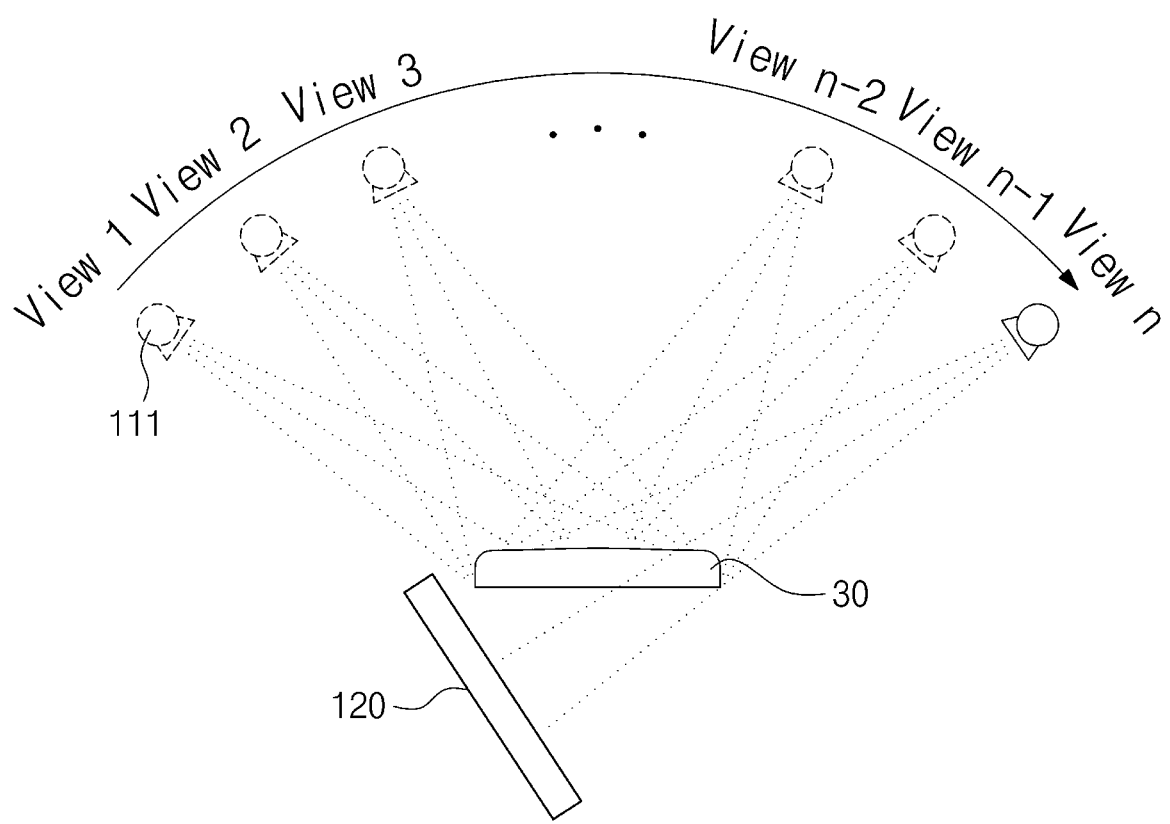
Figure 4D:
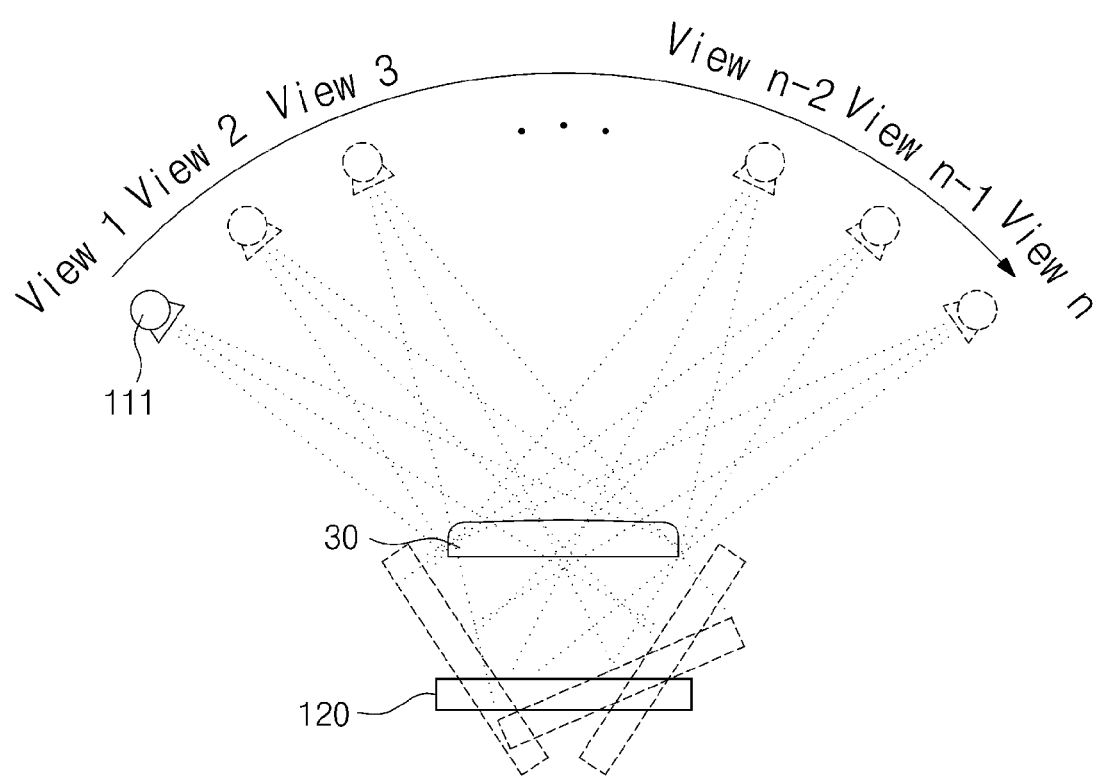

FIG. 3 is a view illustrating an overall external appearance of an X-ray imaging apparatus having a rotatable X-ray detector according to an exemplary embodiment, and FIG. 4 is a view diagrammatically illustrating view variation depending on circular movement of an X-ray source in the X-ray imaging apparatus of FIG. 3.

In the X-ray imaging apparatus 100 of FIG. 3, all of the X-ray source 111, the compression paddle 107, and the X-ray detector 120 are connected to the arm 105 that is connected to the main body 101. Thus, when the arm 105 is rotated about the rotating shaft 103, as illustrated in FIGS. 4A, 4B, 4C, and 4D, the X-ray source 111 and the X-ray detector 120 are rotated together. In this case, difference between neighboring view images is small, which may be advantageous in terms of image processing.

According to the aspect of the X-ray imaging apparatus, there is no limit as to whether or not the X-ray detector is fixed, and both the X-ray imaging apparatus of FIG. 1 and the X-ray imaging apparatus of FIG. 3 may be applied to the exemplary embodiments.

As described above with reference to FIGS. 1 to 4, the X-ray imaging apparatus 100 acquires 2D images corresponding to respective views by emitting X-rays to the object at a plurality of different views, and generates and displays a 3D image of the object using the acquired 2D images, thereby assisting a user in perceiving 3D effects.

In the case in which the object is the breast, a thickness of the object 30 compressed by the compression paddle 107 may be within a range of about 46 to 75 mm, and an average thickness may be about 50 mm. Although there is a slight difference according to a manufacturer, a distance between the X-ray source 111 and the object 30 is usually about 60 cm. Accordingly, the distance between the X-ray source 111 and the object 30 is greater than the thickness of the object 30, which causes the user to perceive somewhat insufficient 3D effects from an image acquired by X-ray emission. This is the same principle as when it may be difficult to perceive 3D effects when viewing a volumetric object from a distance.

Although it may be attempted to increase an interval between views to enhance 3D effects, a distance between human eyes is 6.5 cm on average. Therefore, when increasing the interval between views without considering the distance between human eyes, this may cause a viewer to suffer from dizziness.

Conversely, although it may be considered to reduce the distance between the X-ray source 111 and the object 30, the distance between the X-ray source 111 and the object 30 is set to a value that provides optimized imaging environment in consideration of, e.g., the magnitude of Field of View (FOV) of the X-ray source 111 and the size of the object 30. Therefore, arbitrary reduction in the distance between the X-ray source 111 and the object 30 may cause deterioration of image quality and increase X-ray exposure of the object 30.

Figure 5:
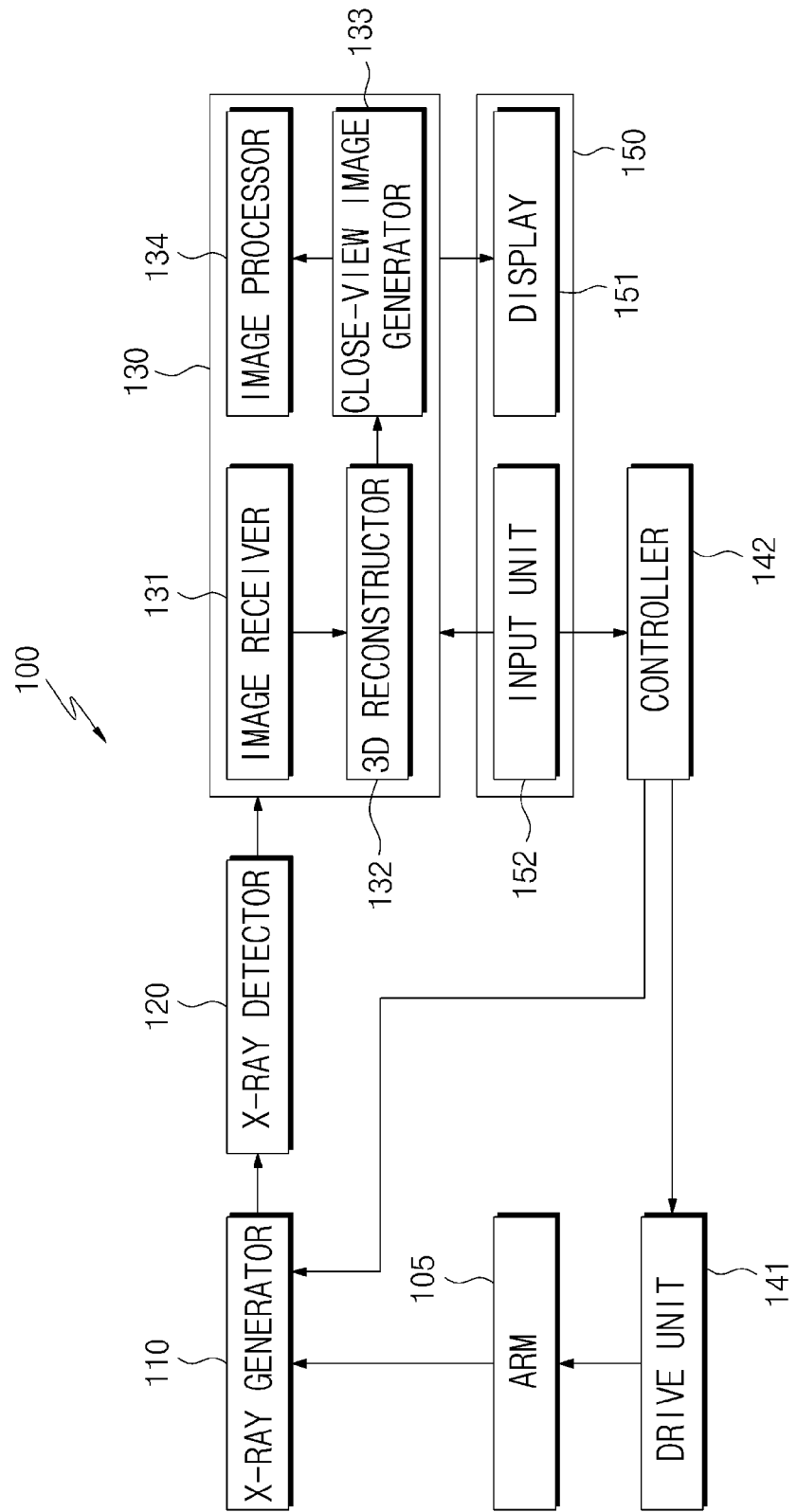
FIG. 5 is a control block diagram of an exemplary embodiment of the X-ray imaging apparatus.

Accordingly, in the X-ray imaging apparatus 100 according to an exemplary embodiment, the distance between the X-ray source 111 and the object 30 may be virtually reduced to enhance 3D effects of a 3D image displayed on the display 151. FIG. 5 is a control block diagram of an exemplary embodiment of the X-ray imaging apparatus.

Referring to FIG. 5, in addition to an X-ray generator 110 and the X-ray detector 120 described above with reference to FIG. 1, the X-ray imaging apparatus 100 includes a drive unit 141 to rotate the arm 105, a controller 142, and an image controller 130 to generate a virtual close-view image of the object.

Hereinafter, operations of respective components of the X-ray imaging apparatus 100 will be described in detail.

The X-ray generator 110 includes the X-ray source 111 to generate and emit X-rays to the object, and a variety of electronic components to generate X-rays. The electronic components to generate X-rays may be mounted in the X-ray source 111 or a housing 101.

Energy of X-rays may be controlled by a tube voltage, and the strength or dose of X-rays may be controlled by a tube current and X-ray exposure duration. The X-ray generator 110 may include a power supplier to generate a tube voltage and tube current. The energy and dose of X-rays emitted from the X-ray generator 110 may be differently set according to the kind of the object, the thickness of the object, a diagnosis purpose, etc.

The X-ray generator 110 may emit monochromatic X-rays or polychromatic X-rays. If the X-ray generator 110 emits polychromatic X-rays having a predetermined energy band, the energy band of X-rays may be defined by upper and lower limits. The upper limit of the energy band, i.e., the maximum energy of X-rays may be adjusted according to the magnitude of a tube voltage, and the lower limit of the energy band, i.e., the minimum energy of X-rays may be adjusted by a filter. The filter serves to pass only X-rays having a particular energy band. Providing the X-ray source 111 with the filter that filters X-rays having a low energy band may raise the lower limit of the energy band, which may increase the average energy of X-rays.

The X-ray detector 120 detects X-rays having passed through the object, and acquires a 2D image of the object from the detected X-rays. More specifically, when X-rays having passed through the object reach the X-ray detector 120, an electric charge is generated according to the energy and dose of X-rays. The X-ray detector 120 converts the electric charge into electric signals to output the electric signals. The electric signals may be converted on a per pixel basis, and an image of the object may be acquired by combining the electric signals of the respective pixels.

The X-ray detector 120 may be classified into a single device and a mixed device according to a material constitution manner thereof, or may be classified into a direct-change mode and an indirect-change mode according to a method of changing detected X-rays into electric signals. In addition, the X-ray generator 120 may be classified into a charge-integration mode and a photon-counting mode according to a method of acquiring electric signals.

If the X-ray detector 120 is of a single device type, a part that detects X-rays and generates electric signals and a part that reads out and processes the electric signals are formed of a single semiconductor material, or are fabricated via a single process. This type of the X-ray detector 120 may be a Charge Coupled Device (CCD) or a Complementary Metal Oxide Semiconductor (CMOS) device.

If the X-ray detector 120 is of a mixed device type, a part that detects X-rays and generates electric signals and a part that reads out and processes the electric signals are formed of different materials, or are fabricated via different processes. For example, this type of the X-ray detector 120 may include a light receiving element, such as a photodiode, a CCD, or a CdZnTe element, to detect X-rays, and a CMOS Read Out Integrated Circuit (CMOS ROIC) to read out and process the electric signals, may include a detection strip to detect X-rays and a CMOS ROIC to read out and process electric signals, or may include an a-Si or a-Se flat panel system.

In the case of the direct-change mode, as electron-hole pairs are generated in the light receiving element when X-rays are emitted and electrons are moved to an anode and holes are moved to a cathode by an electric field applied to both ends of the light receiving element, the X-ray detector 120 changes the movement into electric signals. A constituent material of the light receiving element included in the direct-change mode X-ray detector may be selected from among a-Se, CdZnTe, $HgI_2$, $PbI_2$, etc.

In the case of the indirect-change mode, a scintillator is provided between the light receiving element and the X-ray generator 110 and emits photons having a visible light wavelength in reaction to X-rays emitted from the X-ray generator 110, and the light receiving element detects the photons and changes the photons into electric signals. In the indirect-change mode X-ray detector, for example, the light receiving element is formed of a-Si, and the scintillator is a thin-film shaped GADOX scintillator, or a micro-column type or needle-structured type CSI(T1) scintillator.

In the case of the charge-integration mode, after detected charge is stored for a predetermined time, electric signals are acquired from the charge. In the case of the photon-counting mode, an electric signal is acquired whenever a charge is generated by a single X-ray photon, and the number of photons is counted.

With regard to the X-ray detector 120 of an exemplary embodiment, there is no limit as to material constitution and change and acquisition of electric signals, and any one of the above-described methods may be applied to the X-ray detector 120.

Figure 6:
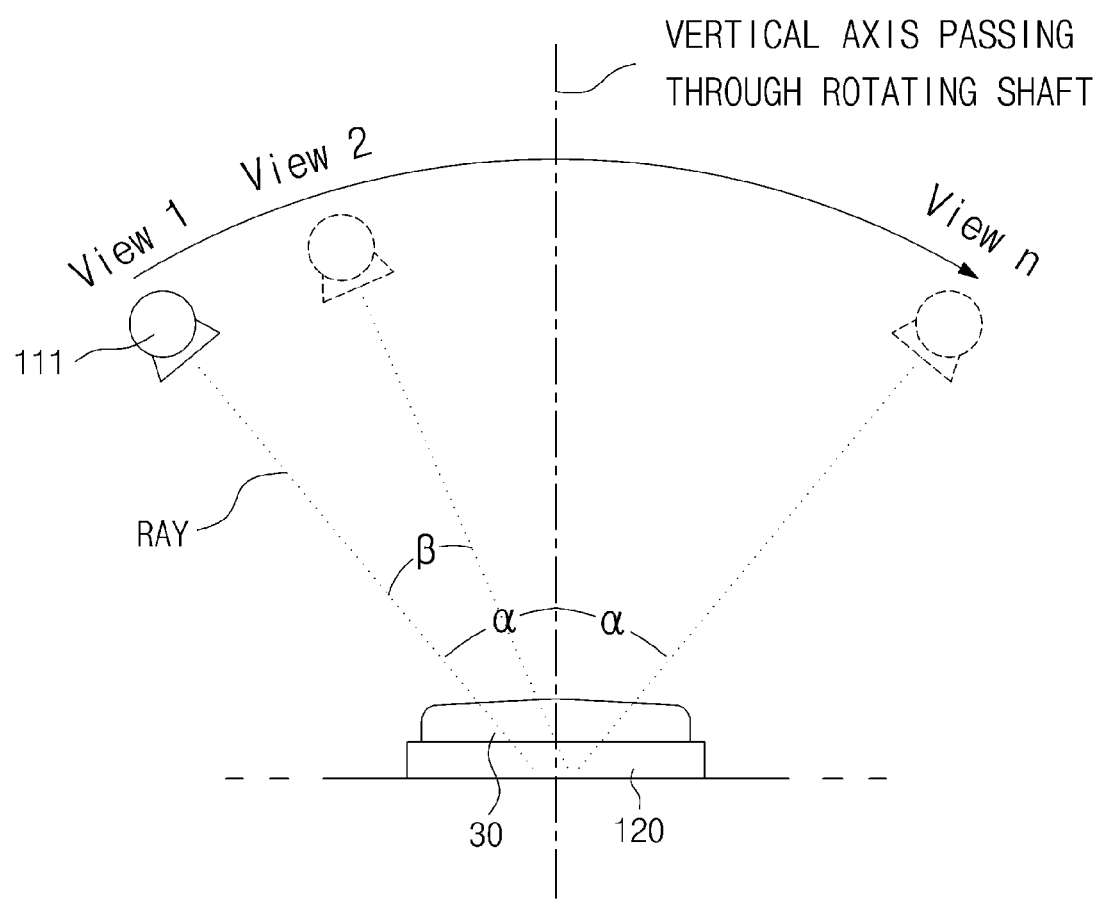
FIG. 6 is a view illustrating an imaging angle and a view interval.

The controller 142 controls the drive unit 141 and the X-ray generator 110 according to imaging conditions, such as characteristics of the object, the kind of the display 151, etc. FIG. 6 illustrates an imaging angle and a view interval. Hereinafter, operation of the controller 142 will be described with reference to FIG. 6.

The controller 142 may set an imaging angle and control the drive unit 141 to rotate the arm 105 according to the set angle, thereby controlling an overall view range for emission of X-rays by the X-ray source 111. Here, the imaging angle is a leftward or rightward movement range of the X-ray source 111. In an exemplary embodiment, as illustrated in FIG. 6, the imaging angle is referred to twice the maximum angle $\alpha$ between a vertical axis passing through the rotating shaft 103 and a ray emitted from the center of the X-ray source 111.

Additionally, the controller 142 may control X-ray emission positions of the X-ray generator 110, i.e., a view interval. As illustrated in FIG. 6, the view interval may be defined as an interval between neighboring views, or an angle $\beta$ between center rays emitted from the X-ray source 111 at neighboring views. The view interval may be set in consideration of a distance between the X-ray source 111 and the object 30 and a distance between human eyes. If the distance between the X-ray source 111 and the object 30 is about 60 cm under the assumption that the distance between human eyes is 6.5 cm, the view angle $\beta$ may be set to 6 degrees. Once the view angle is set, the number of views, i.e., the number of imaging operations is determined based on the view interval.

In an exemplary embodiment, if the imaging angle is set to 84 degrees and the view interval is set to 6 degrees, the controller 142 may perform imaging the total number of 15 times at 15 views by emitting X-rays at the interval of 6 degrees while the X-ray source 111 circularly moves within an angular range of 84 degrees. The aforementioned numerical values are approximate values and are given by way of example, and the exemplary embodiments are not limited to the numerical values. An X-ray image may be acquired whenever X-rays are emitted once, i.e., whenever imaging is performed once, and therefore the total number of 15 2D images may be acquired.

The image controller 130 generates virtual close-view images of the object using acquired 2D images, and generates a 3D image of the object from the virtual close-view images to display the 3D image via the display 151.

Hereinafter, a detailed configuration and operation of the image controller 130 will be described.

The image controller 130 includes an image receiver 131 to receive a plurality of 2D images from the X-ray detector 120, a 3D reconstructor 132 to reconstruct a 3D volume of the object from the received 2D images, a close-view image generator 133 to generate close-view images from the 3D volume of the object, and an image processor 134 to generate a 3D image from the close-view images.

The 3D reconstructor 132 performs 3D reconstruction on the volume of the object using a plurality of 2D images acquired at different views. That is, the 3D reconstructor 132 generates 3D volume data regarding the object. 3D reconstruction is a method of reconstructing a volume of the object in a 3D space constituted of voxels using 2D images of the object. Through use of 3D reconstruction, the volume of the object may be reconstructed from a plurality of 2D images. In an exemplary embodiment, any one of known 3D construction methods may be applied.

To discriminate an acquired real image from virtual close-view and middle-view images, in the exemplary embodiments, a 2D image acquired from the X-ray detector 120 may be referred to as an original-view image.

As described above, if a distance between the X-ray source 111 and the object is reduced, enhanced 3D effects may be perceived from a 3D image of the object. Thus, the close-view image generator 133 generates a virtual close-view image by virtually emitting X-rays to the 3D volume of the object at a distance closer to the object 30 than the X-ray source 111.

To this end, the close-view image generator 133 may adopt reprojection. Reprojection is a method of generating a virtual projection image by receiving 3D volume data regarding the object even if X-rays are not directly emitted to the object, setting a condition, such as a position of the X-ray source, a position of the X-ray detector, volume resolution, or the like, and virtually emitting X-rays to the volume of the object under the set condition.

Accordingly, if the 3D reconstructor 132 inputs the generated volume data regarding the object to the close-view image generator 133, the close-view image generator 133 may set a close-view image generation condition including at least one of a virtual X-ray source position, a virtual X-ray detector position, a virtual imaging angle, a virtual view interval, the number of virtual views, and volume resolution, thereby generating a close-view image based on the set condition. Here, the virtual X-ray source position and the virtual X-ray detector position are used to determine a distance between a virtual X-ray source and a volume of the object. The close-view image generation condition may be set by the close-view image generator 132, or may be input by the user via the input unit 152 provided in the workstation 150.

Once the virtual X-ray source position, the virtual X-ray detector position, and the virtual imaging angle are set, the close-view image generator 132 calculates a virtual view interval and the number of virtual views. The virtual imaging angle may be set to be smaller than a real imaging angle, and the virtual view interval is set based on a distance between human eyes. Setting the virtual imaging angle smaller than the real imaging angle serves to prevent reprojection rays from deviating from a real overall view range of the X-ray source 111 in consideration of FOV of the virtual X-ray source. The distance between human eyes (e.g., 6.5 cm) may be set to a default value, and may be input by the user.

Once the virtual X-ray source position, the virtual X-ray detector position, and the distance between human eyes are set, the virtual view interval may be calculated. In turn, the number of virtual views may be calculated from the virtual view interval and the virtual imaging angle. If the calculated virtual view interval and the calculated number of virtual views are set to the close-view image generation condition, the close-view image generator 132 may generate a close-view image corresponding to the condition in the same number as the set number of virtual views.

Figure 7:
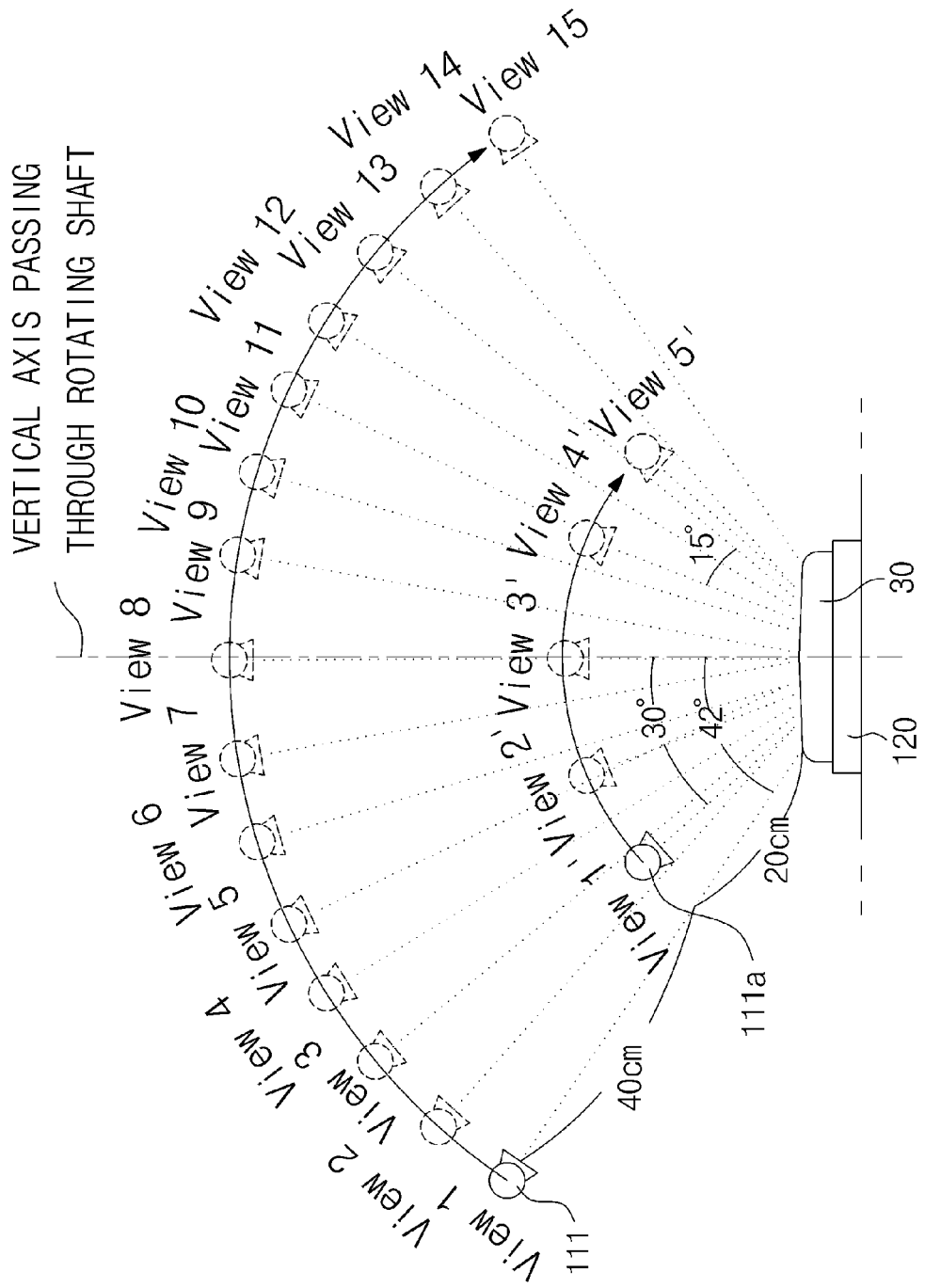
FIG. 7 is a view illustrating virtual view variation for generation of a close-view image.

FIG. 7 is a view illustrating virtual view variation for generation of a close-view image.

Referring to FIG. 7, if the real X-ray source 111 emits X-rays at a position spaced apart from the object 30 by a distance of 60 cm within an imaging angle range of 84 degrees, a thickness of the object 30 is 5 cm, and a view interval is 6 degrees, the X-ray source 111 emits X-rays respectively from view 1 to view 15 while moving from the left side to the right side. The 3D reconstructor 132 performs 3D reconstruction on a volume of the object using 15 2D X-ray images captured at view 1 to view 15. That is, the 3D reconstructor 132 generates 3D volume data regarding the object.

If the generated volume data is input to the close-view image generator 133, the close-view image generator 133 sets a distance between a virtual X-ray source 111a and a 3D volume of the object to 20 cm, and a distance between human eyes is set to 6.5 cm, a calculated virtual view interval is about 15 degrees. If an imaging angle is set to 60 degrees, the close-view image generator 133, as illustrated in FIG. 6, may generate five virtual close-view images that may be acquired when emitting X-rays to the object at five virtual views from view 1' to view 5'.

The image processor 134 generates a 3D image of the object by processing a plurality of close-view images generated by the close-view image generator 133, and displays the 3D image of the object via the display 151. The display 151 may be a 3D display device.

The 3D image of the object may be of a stereoscopic type using binocular disparity, a volumetric type, a holographic type, an integral image type, or the like according to a display method thereof. The stereoscopic type is classified into a stereoscopic type using special glasses and a glasses-free auto-stereoscopic type. The image processor 133 may generate a 3D image of the object using one of the aforementioned methods, and the used method may be changed according to an output format of the display 151.

Figure 8:
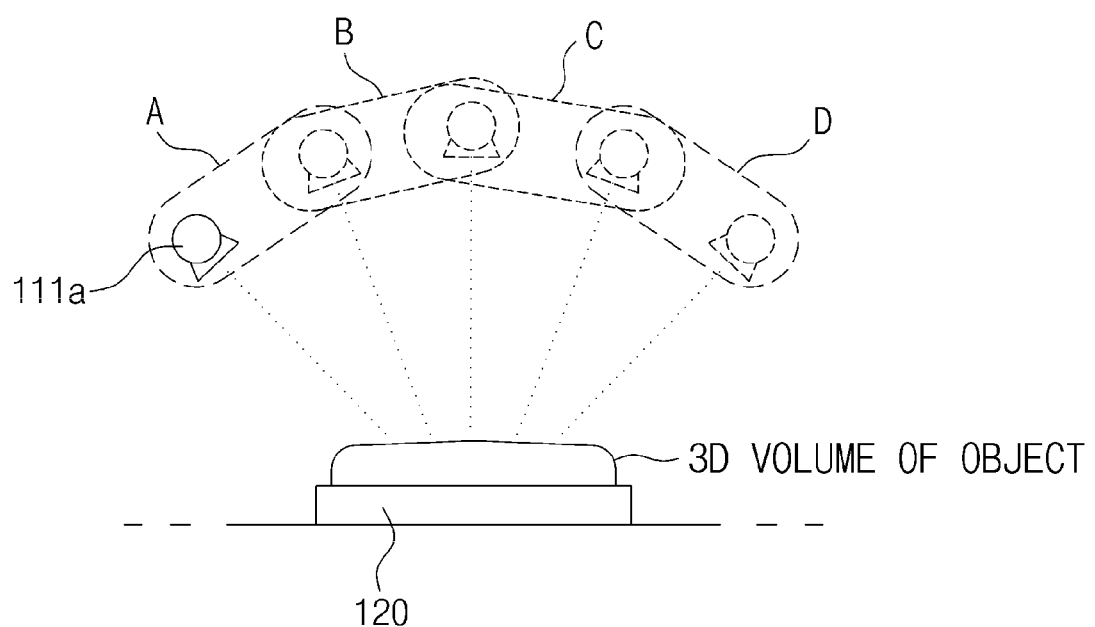
FIG. 8 is a view illustrating a method of generating and displaying a 3D image of an object in a stereoscopic manner.

FIG. 8 is a view illustrating a method of generating and displaying a 3D image of the object in a stereoscopic manner.

As illustrated in FIG. 8, the image processor 134 sets a close-view image corresponding to view 1' and a close-view image corresponding to view 2' to form a pair A, the close-view image corresponding to view 2' and a close-view image corresponding to view 3' to form a pair B, the close-view image corresponding to view 3' and a close-view image corresponding to view 4' to form a pair C, and the close-view image corresponding to view 4' and a close-view image corresponding to view 5' to form a pair D. Then, the image processor 134 synthesizes two close-view images corresponding to one pair in the sequence of A, B, C, and D, and outputs the synthesized images via the display 151. In this case, when the user views the display 151 through special glasses, such as polarized glasses, liquid-crystal shutter glasses, etc., close-view images corresponding to different views are input to both eyes of the user, causing the user to perceive 3D effects. The input images may be images captured at close views, thus providing enhanced 3D effects.

3D image generation via the image processor 134 and display via the display 151 are not limited to the above description, and any other methods may be applied so long as they generate and display a 3D image using a plurality of images corresponding to different views, i.e., a plurality of images captured at different views.

Figure 9:
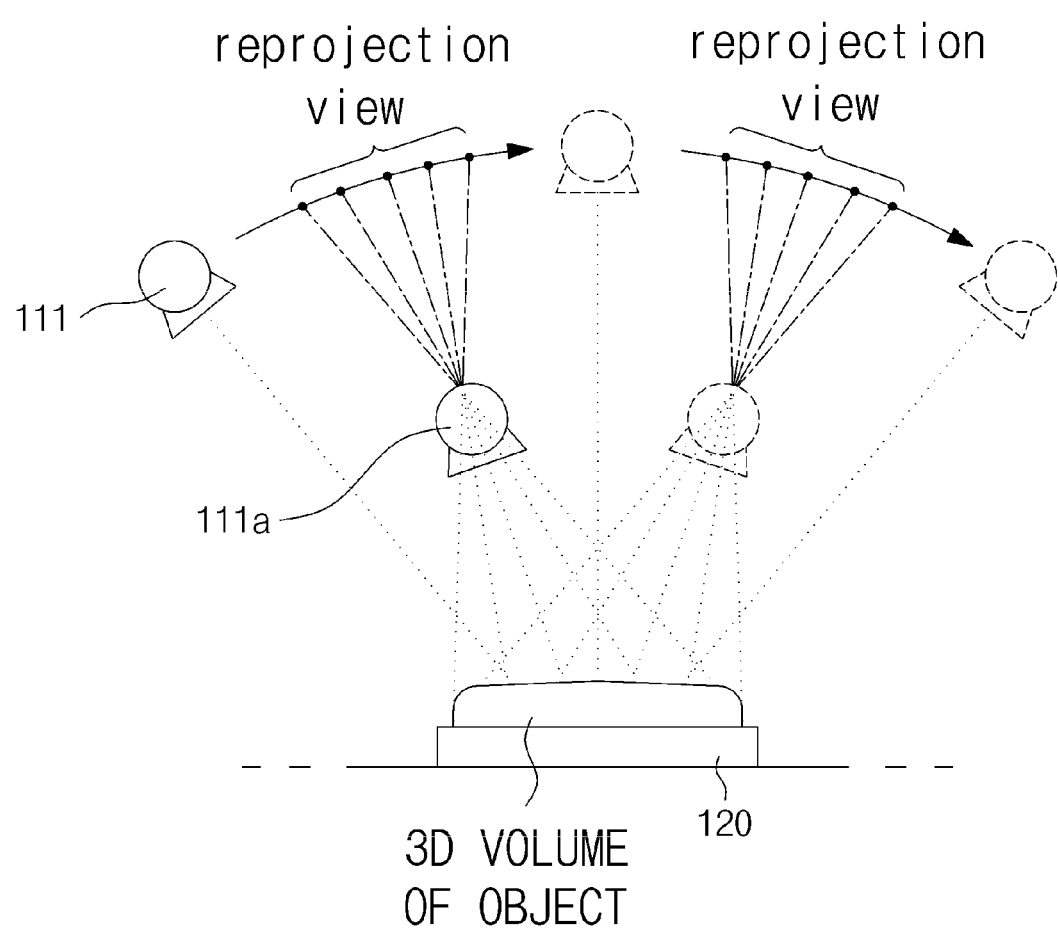
FIG. 9 is a view schematically illustrating projection-ray data for generation of a close-view image.

FIG. 9 is a view schematically illustrating projection-ray data for generation of a close-view image.

A close-view image is generated based on a 3D volume of the object that is captured by the X-ray source 111 and then is reconstructed. Referring to FIG. 9, assuming that the virtual X-ray source 111a emits reprojection rays to a 3D volume of the object, the close-view image generator 133 may generate a less blurred 3D image of the object if 3D volume data regarding the object contains all reprojection ray data.

If some of X-rays used to reconstruct the 3D volume of the object coincide with particular reprojection rays, it can be said that 3D volume data regarding the object contains data regarding the particular reprojection rays.

A reprojection view may be defined as a position where extended reprojection rays meet with a real X-ray source line. Since an interval between original-view positions at which the real X-ray source 111 emits X-rays is not dense, the original-view positions may make it difficult to acquire all of the 2D images at reprojection views. Therefore, in another embodiment of the X-ray imaging apparatus, middle-view images corresponding to middle view positions located between original-view positions may be generated and used to reconstruct a 3D volume of the object, which may minimize blurring of a 3D image of the object.

Figure 10:
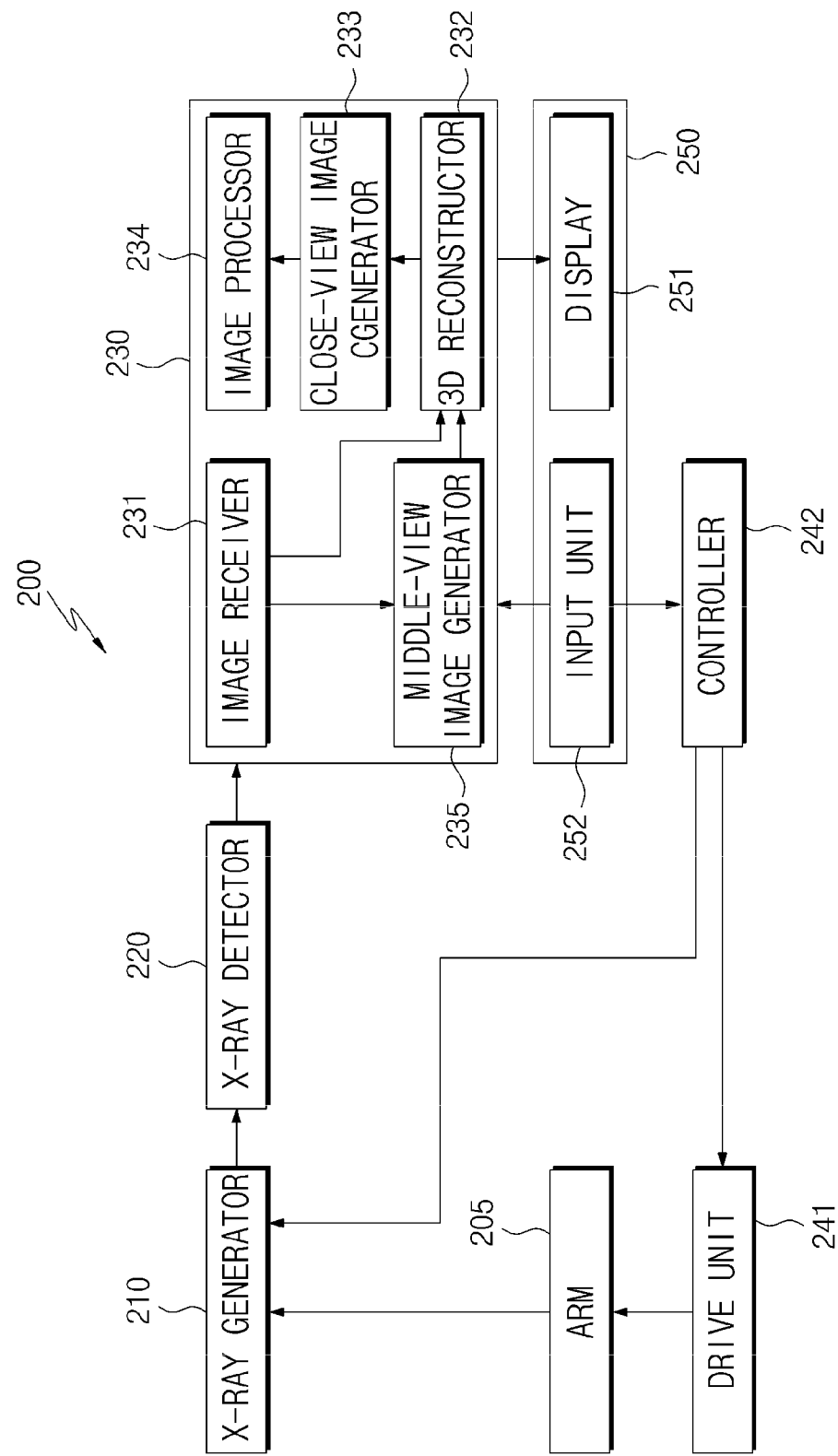
FIG. 10 is a control block diagram of an X-ray imaging apparatus according to another embodiment.

FIG. 10 is a control block diagram of an X-ray imaging apparatus according to another embodiment.

Referring to FIG. 10, in another embodiment of the X-ray imaging apparatus, an image controller 230 includes an image receiver 231 to receive a plurality of original-view images from an X-ray detector 220, a middle-view image generator 235 to generate middle-view images from the received original-view images, a 3D reconstructor 232 to reconstruct a 3D volume of the object from the original-view images acquired from the X-ray detector 220 and the middle-view images, a close-view image generator 233 to generate close-view images of the object by virtually emitting X-rays to the 3D volume of the object, and an image processor 234 to generate a 3D image from the close-view images.

A description of an X-ray generator 210, the X-ray detector 220, a drive unit 241, a controller 242, a display 251, and an input unit 252 is equal to the above description, and a detailed description thereof is omitted herein.

The middle-view image generator 235 generates virtual 2D images at middle views between original-view positions. Widely known methods of generating middle-view images may include an average method between neighboring view images, a directional interpolation method, and a reprojection method, for example. Alternatively, a method of reconstructing a 3D volume of the object, predicting motion of the reconstructed 3D volume, and generating middle images between 2D images of the object, i.e., middle-view images based on the predicted motion may be possible. The middle-view image generator 235 may adopt any one of various methods of generating middle-view images between views at which imaging is actually performed.

The generated middle-view images are input to the 3D reconstructor 232 along with the original-view images acquired from the X-ray detector 220. The 3D reconstructor 232 reconstructs a 3D volume of the object using the original-view images and the middle-view images. To this end, a 3D reconstruction method is applied.

The 3D volume data of the object is input to the close-view image generator 233. The close-view image generator 233 may set a close-view image generation condition including a virtual X-ray source position, a virtual X-ray detector position, a virtual imaging angle, a virtual view interval, the number of virtual views, volume resolution, or the like, thereby generating a close-view image based on the set condition. Here, the virtual X-ray source position and the virtual X-ray detector position are used to determine a distance between a virtual X-ray source and a volume of the object. The close-view image generation condition may be set by the close-view image generator 232, or may be input by the user via the input unit 252 provided in a workstation 250.

Once the aforementioned conditions are set, the close-view image generator 232 calculates a virtual view interval and the number of virtual views. The virtual imaging angle may be set to be smaller than a real imaging angle, and the virtual view interval is set based on a distance between human eyes. The distance between human eyes (e.g., 6.5 cm) may be set to a default value, and may be input by the user. Once the virtual X-ray source position, the virtual X-ray detector position, and the distance between human eyes are set, the virtual view interval may be calculated. In turn, the number of virtual views may be calculated from the virtual view interval and the virtual imaging angle. If the calculated virtual view interval and the calculated number of virtual views are set to the close-view image generation conditions, the close-view image generator 232 may generate close-view images corresponding to the set conditions, i.e., close-view images acquirable when performing X-ray imaging under the set conditions in the same number as the set number of virtual views.

The image processor 234 generates a 3D image of the object by processing the generated close-view images. As exemplified in the above-described embodiment, neighboring close-view images may be synthesized to form a pair, or a plurality of close-view images may be subjected to weaving via a multi-view imaging method. As the resulting image is displayed via the display 251, perception of a 3D image without wearing special glasses may be possible. The 3D image displayed via the display 251 contains data regarding dense middle-view images, and therefore viewing images while continuously varying views may be possible, which results in enhanced 3D effects of the displayed 3D image.

Although the above embodiments have been described based on the X-ray imaging apparatus, the above-described 3D image generation method may be applied to general 3D imaging apparatuses except for the X-ray imaging apparatus.

Figure 11:
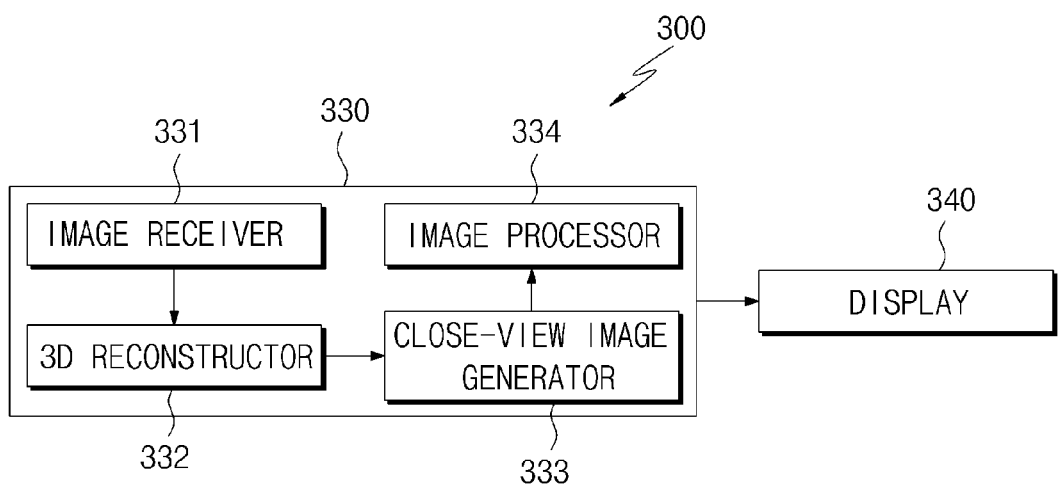
FIG. 11 is a control block diagram of a 3D imaging apparatus according to an exemplary embodiment.

FIG. 11 is a control block diagram of a 3D imaging apparatus according to an exemplary embodiment.

Referring to FIG. 11, according to an exemplary embodiment, the 3D imaging apparatus 300 includes an image processor 330 that includes an image receiver 331 to receive a plurality of original-view images captured at a plurality of different views using an image acquisition device, such as a camera, a 3D reconstructor 332 to reconstruct a 3D volume of the object using the received the original-view images, a close-view image generator 333 to generate close-view images from the reconstructed 3D volume of the object, and an image processor 334 to generate a 3D image from the close-view images, and a display 340 to display the generated 3D image in a 3D manner.

The image acquisition device may be a general camera, such as a CCD camera or a CMOS camera, for example, and may capture real images of the object at a plurality of different views. The image acquisition device may acquire virtual images of the object like images captured at a plurality of different views using a computer program. Original-view images acquired by the image acquisition device are 2D images, and are input to the image receiver 331.

Operations of the 3D reconstructor 332, the close-view image generator 333, and the image processor 334 are equal to those in the exemplary embodiment of FIG. 5.

Explaining the operations in brief, the 3D reconstructor 332 performs 3D reconstruction on a volume of the object using a plurality of 2D images acquired at different views. That is, 3D volume data regarding the object is generated.

The close-view image generator 333 generates virtual close-view images assuming that the reconstructed 3D volume of the object is captured at a shorter distance than a real imaging distance.

The generated close-view images are input to the image processor 334 such that a 3D image is displayed via the display 340.

The 3D imaging apparatus 300 may be applied to a medical appliance, such as an X-ray imaging apparatus, an ultrasound imaging apparatus, etc., as well as general imaging apparatuses. Any one device may serve as the 3D imaging apparatus 300 so long as such device generates and displays a 3D image using images directly captured at different views, or virtual images simulating images captured at different views.

Hereinafter, an exemplary embodiment of an X-ray image generation method will be described with reference to the drawings.

Figure 12:
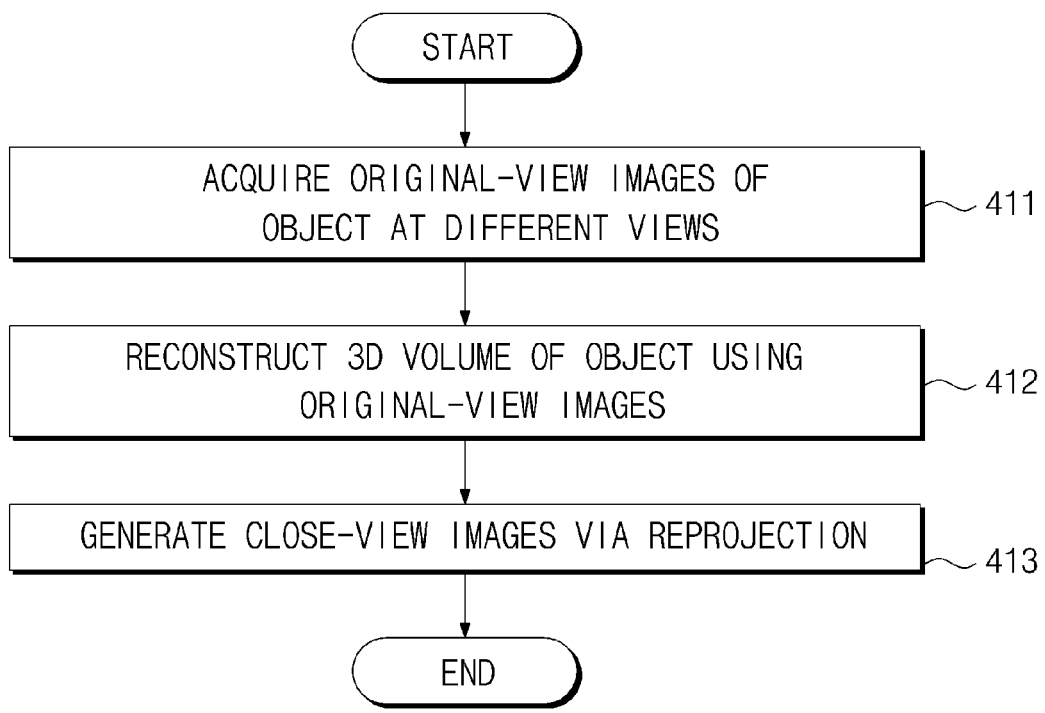
FIG. 12 is a flowchart illustrating an exemplary embodiment of generation of a close-view image in an X-ray image generation method.

FIG. 12 is a flowchart illustrating an exemplary embodiment of generation of a close-view image in the X-ray image generation method.

Referring to FIG. 12, first, X-rays are emitted to an object at different views to acquire original-view images of the object (operation 411). The original-view images are 2D images acquired by emitting X-rays to the object at respective original views and detecting X-rays having passed through the object. Positions and the number of original views may be set in consideration of an imaging angle and a distance between human eyes.

Next, a 3D volume of the object is reconstructed using the plurality of original-view images (operation 412). In this case, reconstruction of the 3D volume of the object from the plurality of original-view images may be performed using a 3D reconstruction method. In one example, an iterative reconstruction method may be applied.

Next, a plurality of close-view images is generated by virtually emitting X-rays to the volume of the object at a shorter distance than a real distance via reprojection (operation 413). Reprojection is a method of generating a virtual projection image by setting a condition, such as 3D volume data regarding the object, a position of the X-ray source, a position of the X-ray detector, volume resolution, or the like, even if X-rays are not directly emitted to the object, and virtually emitting X-rays to the object under the set condition. As described above, if a distance between the X-ray source and the object is reduced, enhanced 3D effects may be perceived from a 3D image of the object. Thus, the close-view images are generated under the assumption that the virtual X-ray source is located closer to the object than the real X-ray source.

Figure 13:
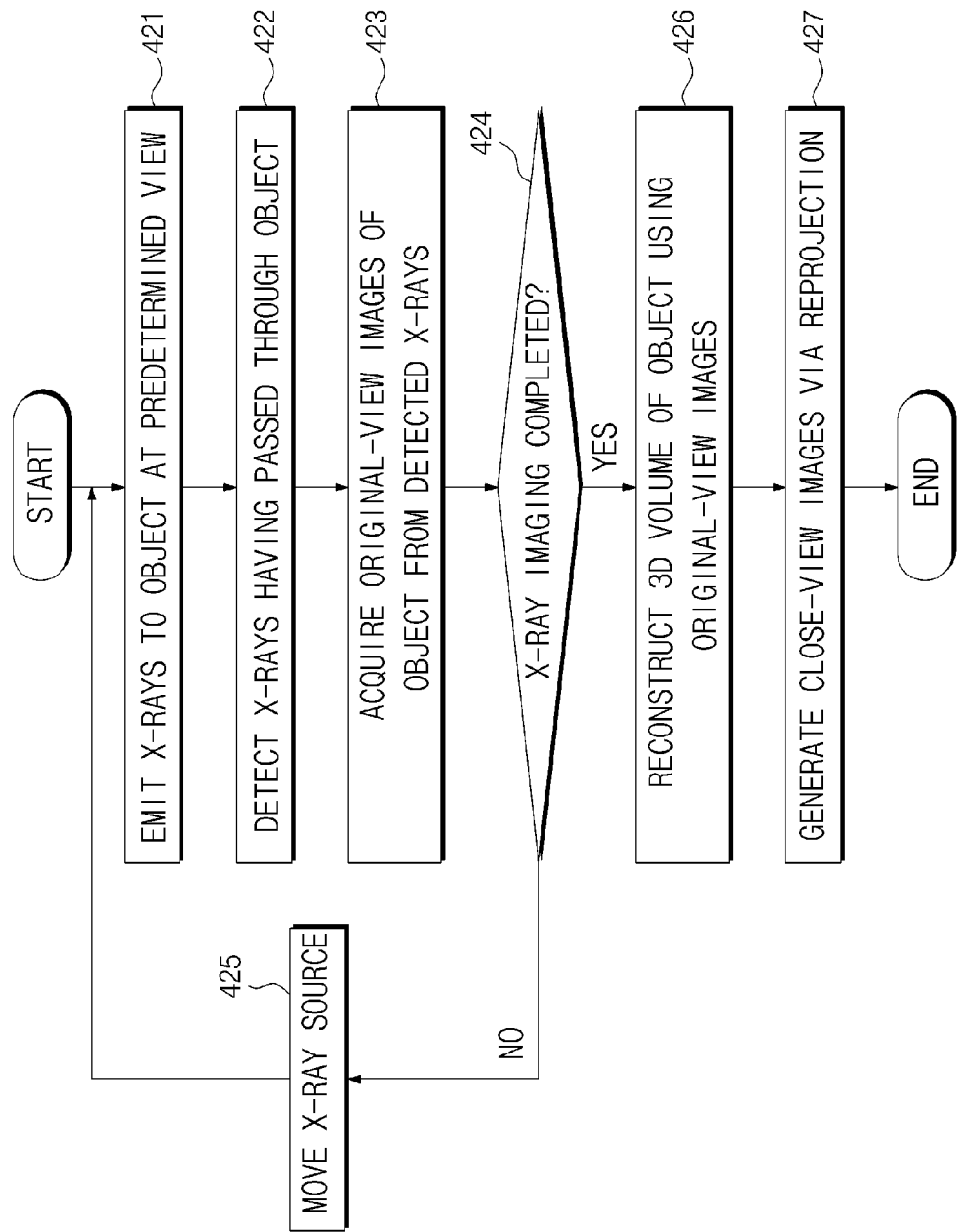
FIG. 13 is a flowchart illustrating acquisition of original-view images in the embodiment of FIG. 12.

FIG. 13 is a flowchart illustrating acquisition of original-view images in the exemplary embodiment of FIG. 12.

Referring to FIG. 13, X-rays are emitted to an object at a predetermined view (operation 421), X-rays having passed through the object are detected (operation 422), and 2D images, i.e., original-view images of the object are acquired from the detected X-rays (operation 423).

Then, it is judged whether or not X-ray imaging is completed (operation 424). When the X-ray source emits X-rays at all preset views within an imaging angle range, completion of X-ray imaging may be judged. X-ray emission views may be determined in consideration of an imaging angle, a thickness of the object, a distance between the X-ray source and the object, and a distance between human eyes. Referring to the illustration of FIG. 7, if the X-ray source 111 emits X-rays within an imaging angle of 84 degrees at a position spaced apart from the object 30 by a distance of 60 cm, a thickness of the object 30 is 5 cm, and a view interval is 6 degrees, completion of X-ray imaging may be determined when X-rays are completely emitted respectively at view 1 to view 15.

If X-ray imaging is not completed (No in Operation 424), a procedure of moving the X-ray source to next view (operation 425) to again emit X-rays to the object and acquire an original-view image is repeated.

If X-ray imaging is completed (Yes in Operation 424), a 3D volume of the object is reconstructed using a plurality of original-view images (operation 426), and a plurality of close-view images is generated by virtually emitting X-rays to a volume of the object at a shorter distance than a real distance via reprojection (operation 427). Reprojection has been described above.

Figure 14:
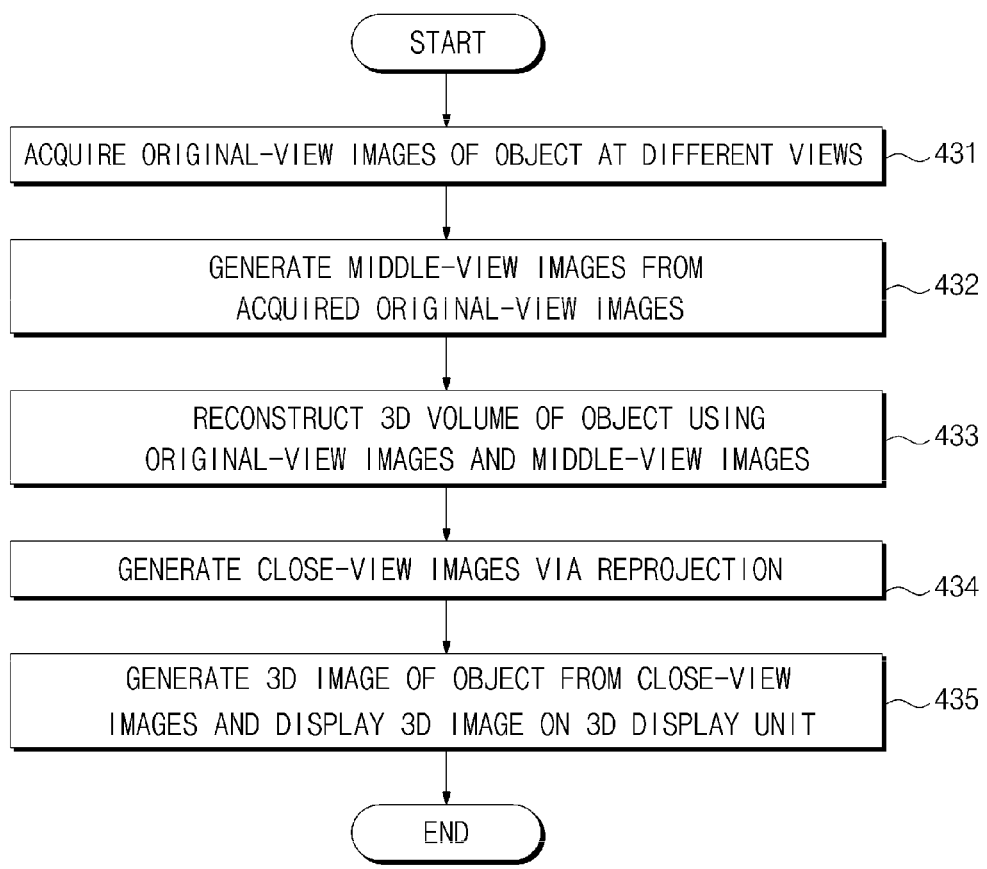
FIG. 14 is a flowchart illustrating an exemplary embodiment of an X-ray image generation method.

FIG. 14 is a flowchart illustrating an exemplary embodiment of an X-ray image generation method.

Referring to FIG. 14, a plurality of original-view images of an object is acquired by emitting X-rays to the object at different views (operation 431). Then, middle-view images are generated using the acquired original-view images (operation 432). The middle-view images are virtual 2D images generated under the assumption that X-rays are emitted to the object at middle views between original views. The middle-view images serve to reduce blurring of a final 3D image of the object. The middle-view images have been described above with reference to FIG. 10, and a detailed description thereof will be omitted hereinafter.

A 3D volume of the object is reconstructed using the original-view images and the virtual middle-view images (operation 433), and a plurality of close-view images is generated by virtually emitting X-rays to a volume of the object at a shorter distance than a real distance via reprojection (operation 434).

A 3D image of the object is generated from the plurality of close-view images, and is displayed on a 3D display (operation 435). The 3D image may be a stereoscopic image, a volumetric image, a holographic image, an integral image type, or the like, and the type of the 3D image may be determined according to an output format of the display. In an exemplary embodiment, if the output format of the display is of a stereoscopic type using polarized glasses, neighboring close-view images may be synthesized to form a pair and be sequentially displayed via the display. If the output format of the display is of a multi-view image type as one example of an auto-stereoscopic type, a plurality of close-view images may be subjected to weaving and be displayed via the display.

As apparent from the above description, according to an exemplary embodiment of an X-ray imaging apparatus, virtual close-view images are generated under the assumption that X-rays are emitted to an object at a shorter distance than a real distance, whereby a 3D X-ray image having enhanced 3D effects may be generated using the generated close-view images.

The described-above exemplary embodiments and advantages are merely exemplary and are not to be construed as limiting. The present teaching can be readily applied to other types of apparatuses. The description of exemplary embodiments is intended to be illustrative, and not to limit the scope of the claims, and many alternatives, modifications, and variations will be apparent to those skilled in the art.

What is claimed is:

1. An X-ray imaging apparatus comprising:
    an X-ray source configured to emit X-rays to an object at different original-view positions;
    an X-ray detector configured to detect the X-rays having passed through the object to acquire original-view images corresponding to respective original-view positions; and
    an image controller configured to reconstruct a three-dimensional (3D) volume of the object from the original-view images and generate close-view images by virtually emitting X-rays to the 3D volume of the object from a shorter distance than a distance between the X-ray source and the object.

2. The apparatus according to claim 1, wherein the image controller includes:
    a 3D reconstructor configured to reconstruct the 3D volume of the object from the original-view images by using a 3D reconstruction method.

3. The apparatus according to claim 2, wherein the image controller further includes:
    a close-view image generator configured to generate the close-view images by virtually emitting the X-rays to the 3D volume of the object from the shorter distance than the distance between the X-ray source and the object via reprojection.

4. The apparatus according to claim 1, wherein the image controller includes:
    a middle-view image generator configured to generate middle-view images corresponding to middle view positions located between the original-view positions.

5. The apparatus according to claim 4, wherein the image controller further includes:
    a 3D reconstructor configured to reconstruct the 3D volume of the object from the original-view images and the middle-view images using a 3D reconstruction method.

6. The apparatus according to claim 5, wherein the image controller further includes:
    a close-view image generator configured to generate the close-view images by virtually emitting X-rays to the 3D volume of the object from the shorter distance than the distance between the X-ray source and the object via reprojection.

7. The apparatus according to claim 3, wherein the close-view image generator is configured to receive the 3D volume of the object from the 3D reconstructor, set a close-view image generation condition, and generate the close-view images via the reprojection based on the close-view image generation condition.

8. The apparatus according to claim 7, wherein the close-view image generation condition includes at least one of a position of a virtual X-ray source, a position of a virtual X-ray detector, a virtual imaging angle, a virtual view interval, a number of virtual views, and volume resolution.

9. The apparatus according to claim 3, further comprising:
    an image processor configured to generate a 3D image of the object using the close-view images.

10. The apparatus according to claim 9, further comprising:
    a display configured to display the 3D image generated by the image processor in a 3D manner.

11. The apparatus according to claim 10, wherein the image processor configured to generate a stereoscopic or an auto-stereoscopic image from the close-view images.

12. An X-ray image generation method comprising:
    emitting X-rays to an object at different original-view positions;
    detecting the X-rays having passed through the object;
    acquiring original-view images corresponding to respective original-view positions, based on the detected X-rays;
    reconstructing a three-dimensional (3D) volume of the object from the original-view images; and
    generating close-view images by virtually emitting X-rays to the 3D volume of the object from a shorter distance than an X-ray emission distance to the object from the original-view positions.

13. The method according to claim 12, further comprising:
    generating middle-view images corresponding to middle view positions located between the original-view positions, from the original-view images.

14. The method according to claim 13, wherein the reconstructing the 3D volume includes:
    reconstructing the 3D volume of the object by using the original-view images and the middle-view images.

15. The method according to claim 12, wherein the generating the close-view images includes:
    setting a close-view image generation condition; and generating the close-view images via reprojection based on the close-view image generation condition.

16. The method according to claim 15, wherein the close-view image generation condition includes at least one of a position of a virtual X-ray source, a position of a virtual X-ray detector, a virtual imaging angle, a virtual view interval, a number of virtual views, and volume resolution.

17. The method according to claim 12, further comprising: generating a 3D image of the object using the close-view images.

18. The method according to claim 17, further comprising: displaying the 3D image of the object on a 3D display.

19. The method according to claim 18, wherein the generating the 3D image of the object includes generating a stereoscopic or an auto-stereoscopic image from the close-view images.

20. A three-dimensional (3D) imaging apparatus comprising:
an image receiver configured to receive original-view images acquired at different original-view positions;
a 3D reconstructor configured to reconstruct a 3D volume of an object from the original-view images; and
a close-view image generator configured to generate virtual close-view images based on an imaginable object corresponding to the 3D volume of the object, by virtually positioning the imaginable object at a shorter distance from a virtual X-ray source than an actual distance between each original-view position and the object; and
an image processor configured to generate a 3D image of the object using the close-view images.

* * * * *